United States Patent [19]
Wolf

[11] Patent Number: 5,554,780
[45] Date of Patent: Sep. 10, 1996

[54] PROCESS FOR THE PREPARATION OF 1-(3-TRIALKYLSILYLPHENYL)-2,2,2-TRIFLUOROMETHYL ETHANONE DERIVATIVES

[75] Inventor: Richard A. Wolf, Midland, Mich.

[73] Assignee: Merrell Pharmaceuticals Inc., Cincinnati, Ohio

[21] Appl. No.: 382,949

[22] Filed: Feb. 1, 1995

Related U.S. Application Data

[63] Continuation of Ser. No. 238,768, May 5, 1994, abandoned.

[51] Int. Cl.$^6$ .................. C07F 7/08; C07F 7/18
[52] U.S. Cl. ............................................. 556/436
[58] Field of Search ................................ 556/436

[56] References Cited

U.S. PATENT DOCUMENTS 4,536,265   8/1985   Fabrizio et al. .................... 556/436 X

FOREIGN PATENT DOCUMENTS 0403713   12/1990   European Pat. Off. .
0409676   1/1991   European Pat. Off. .

OTHER PUBLICATIONS

Chemical Abstracts, vol. 113:211573d (1990).
Chemical Abstracts, vol. 115:158879w (1991).
Simons, J. H. et al, *JACS*, vol. 65, pp. 389–392 (Mar. 1943).
Cohen S. G. et al., *JACS*, vol. 71, pp. 3439–3440 (Oct. 1949).
Kerdesky, A. A. J. et al., *Tetrahedron Letters*, vol. 32, pp. 2003–2004 (1991).
Yamakawa, T. et al, *J. Med Chem* 1990, vol. 33 pp. 1430–1437.
Effenberger F. et al., *Angew. Chem Int* Ed. Engl., vol. 20, pp. 265–266 (1981).
Koser, G. F. et al., *J. Org. Chem.*, vol. 45, pp. 1543–1544 (1980).
Sniekus, V. *Chem. Rev.*, vol. 90, pp. 879–933 (1990).

Primary Examiner—Paul F. Shaver
Attorney, Agent, or Firm—Nelsen L. Lentz

[57] ABSTRACT

The present invention relates to a novel process for preparing 1-(3-trialkylsilylphenyl)-2,2,2-trifluoromethyl ethanones which are useful for the treatment of Alzheimer's disease and senile dementia as disclosed by Schirlin, et al. in European Patent Application Publication No. 0 409 676, published Jan. 23, 1991.

5 Claims, No Drawings

PROCESS FOR THE PREPARATION OF 1-(3-TRIALKYLSILYLPHENYL)-2,2,2-TRIFLUOROMETHYL ETHANONE DERIVATIVES

This is a continuation of application Ser. No. 08/238,768, filed May 5, 1994, which is herein incorporated by reference, now abandoned.

BACKGROUND OF THE INVENTION

The present invention relates to a novel process for preparing 1-(3-trialkylsilylphenyl)-2,2,2-trifluoromethyl ethanones which are useful for the treatment of Alzheimer's disease and senile dementia as disclosed by Schirlin, et al. in European Patent Application Publication No. 0 409 676, published Jan. 23, 1991.

SUMMARY OF THE INVENTION

The present invention provides a novel process for the preparation of a compound of formula (I):

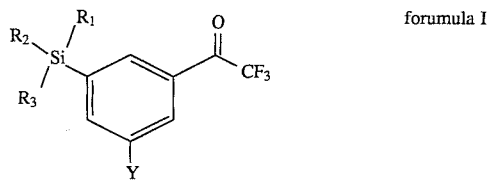

forumula I wherein $R_1$, $R_2$ and $R_3$ are each independently $C_1$–$C_4$ alkyl; and Y is hydrogen or —$SiR_1R_2R_3$, comprising reacting a compound of the formula (II):

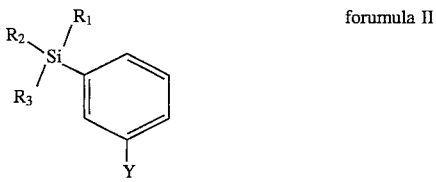

forumula II wherein $R_1$, $R_2$, $R_3$ and Y are defined as above, with a trifluoroacylating agent in the presence of a Friedel-Crafts acylating catalyst.

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. The terms "halo", "halogen" or "halide" refer to a chlorine, bromine or iodine atom.

The process of the present invention is set forth in Scheme I. All the substituents, unless otherwise indicated are previously defined. The reagents and starting materials are readily available to one of ordinary skill in the art.

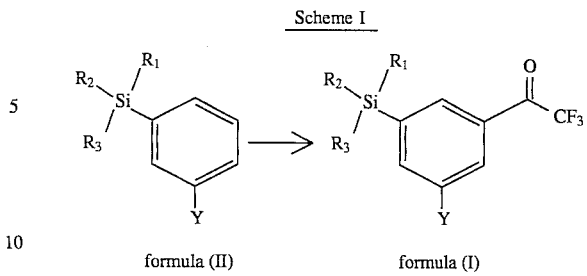

Scheme I formula (II)   formula (I)

In Scheme I, the silylated phenyl compound of formula (II) can be converted to the desired final compound of formula (I) as described generally below.

A Friedel-Crafts acylating catalyst is combined with a suitable organic solvent at a suitable reaction temperature with stirring. Examples of Friedel-Crafts acylating catalysts are aluminum chloride, or mixtures of Friedel-Crafts acylating catalysts, such as ferric chloridealuminum chloride and the like. The preferred Friedel-Crafts acylating catalyst is aluminum chloride. Suitable organic solvents are those which are generally used for Friedel-Crafts reactions, such as methylene chloride, cyclohexane, heptane, octane, methylcyclohexane, dichloroethane and the like. The preferred organic solvent is methylene chloride or cyclohexane. A suitable reaction temperature is from about −100° to 100° C. The preferred reaction temperature is from about −70° to 25° C. and the most preferred reaction temperature is from about −50° to 0° C. A solution of a suitable trifluoroacylating agent in a suitable organic solvent is added to the slurry either dropwise or in a steady stream. Examples of suitable trifluoroacylating agents are trifluoroacetic anhydride, mixed anhydrides such as trifluoroacetyl triflate, trifluoroacetyl halides such as trifluoroacetyl chloride and the like. The preferred trifluoroacylating agents are trifluoroacetic anhydride and trifluoroacetyl chloride and the most preferred trifluoroacylating agent is trifluoroacetic anhydride.

After addition of the solution of trifluoroacylating agent is complete, a solution of the silylated phenyl compound of formula (II) in a suitable organic solvent is added dropwise or in a steady stream to the slurry. The molar ratio of Friedel-Crafts acylating catalyst to the silylated phenyl compound of formula (II) can be varied from about 0.25 to greater than 3.0, and the preferred molar ratio is about 0.80 to 2.0. In addition, the molar ratio of trifluoroacylating agent to the silylated phenyl compound of formula (II) can be varied from about 0.10 to greater than 5.0. The preferred molar ratio of trifluoroacylating agent to the silylated phenyl compound of formula (II) is about 0.30 to 2.0 and the most preferred is 0.50 to 1.0. The reaction is then allowed to stir for 30 minutes to 3.5 days. The reaction is then quenched, the product is isolated and then purified using techniques well known to one of ordinary skill in the art to provide the compounds of formula (I). For example, the reaction can be poured into cold water with mixing. The aqueous layer is then extracted with a suitable organic solvent, such as methylene chloride or hexane. The combined organic extracts are rinsed with water, dried over anhydrous magnesium sulfate, filtered and concentrated under vacuum. The residue can then be purified by chromatography, such as gas or flash chromatography, or by distillation to provide the compounds of formula (I).

The following examples present typical process as described in Scheme I. These examples are understood to be illustrative only and are not intended to limit the scope of the present invention in any way. As used herein, the following terms have the indicated meanings: "g" refers to grams; "mmol" refers to millimoles; "ml" refers to milliliters; "bp" refers to boiling point; "mp" refers to melting point; "°C" refers to degrees Celsius; "mm Hg" refers to millimeters of mercury; "µL" refers to microliters; "µg" refers to micrograms; "R$_t$" refers to retention time; "min" refers to minutes and "µM" refers to II micromolar.

EXAMPLE 1

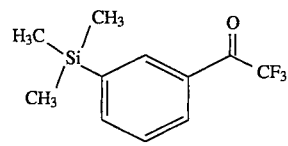

Preparation of
1-(3-trimethylsilylphenyl)-2,2,2-trifluoromethyl
ethanone in methylene chloride.

To a 100 mL three-necked, round-bottomed flask, with thermometer in one side arm and calcium chloride-filled drying tube in the other side arm, add aluminum chloride (2.94 g, 22 mmol) and methylene chloride (30 mL). Cool the slurry in an ice/water bath to 6° C. Add a solution of trifluoroacetic anhydride (2.20 g, 11 mmol) in 8 mL methylene chloride to the stirred (by magnetic bar) slurry by Pasteur pipet. The temperature of the resulting slurry increases during this addition to 8° and then falls back to 4° C. Add a solution of phenyltrimethylsilane (1.50 g, 10 mmol) in 10 mL methylene chloride, from an addition funnel, to the stirred slurry over a period of 45 minutes, keeping the temperature of the reaction mixture at 4° to 5° C. Wash the addition funnel with another 3 mL methylene chloride, which is added to the reaction mixture. Allow the reaction mixture to stir for another 30 minutes at 4° to 10° C. and then allow the reaction mixture to warm to ambient temperature and stir at ambient for 3.5 days. During the ambient temperature stir, the mixture had turned into a dark, thick brown mixture. Removal of an aliquot of this mixture and analysis by gas chromatography yields the following (amounts expressed as peak area percents): trifluoroacetophenone (39.7%, R$_t$=1.67 minutes), 1-(3-trialkylsilylphenyl)-2,2,2-trifluoromethyl ethanone (39.6%, R$_t$=5.10), 1-(4-trialkylsilylphenyl)-2,2,2-trifluoromethyl ethanone (20.2%, R$_t$=5.62 minutes); bp of title compound=120° C. at 14 mm Hg; estimated bp of title compound=126° C. at 20 torr and 242° C. at 760 torr; estimated bp of 1-(4-trialkylsilylphenyl)-2,2,2-trifluoromethyl ethanone=c.a. 131° C. at 20 torr and c.a. 250° C. at 760 torr.

EXAMPLE 1a

Larger scale preparation of
1-(3-trimethylsilylphenyl)- 2,2,2-trifluoromethyl
ethanone in cyclohexane.

Charge a 250 mL three-necked round-bottomed flask fitted with a magnetic stirring bar, thermometer (in one side arm), calcium chloride-filled drying tube (in the other side arm) and an addition funnel (in the center neck) with aluminum chloride (32.00 g, 240 mmol). Cool the flask to −10° C. with a dry ice/ethylene glycol bath, and add trifluoroacetic anhydride (25.20 g, 120 mmol) by pipet quickly to the flask. The temperature of the resulting solid plug rises to +10° C. Add cyclohexane (4 mL) and break up the solid plug into finer particles. While the slurry is cooled and stirred, add neat phenyltrimethylsilane (45.00 g, 300 mmol) via the addition funnel, over an eleven minute period. Rinse the addition funnel with another 4 mL cyclohexane, and add this rinse to the reaction slurry.

Stir the resulting slurry vigorously by magnetic bar, to break up the solids into finer particles. Stir the reaction slurry at −10° C. for 340 minutes. Allow the reaction slurry to warm to ambient temperature over a 30 minute period, during which time the slurry turns a darker color. Put an ice/water bath under the reaction flask, for one hour, prior to working up the reaction.

Pour the thick black reaction slurry into 250 g ice/water mixture in a 500 mL Erlenmeyer flask, and cool with an ice/water bath. The temperature of the resulting slurry rises to about 22° C. Rinse the reaction flask with 150 mL hexane, and add this rinse to the chilled reaction mixture/water slurry. Stir the resulting slurry thoroughly by magnetic bar. Allow the mixture (top organic layer dark brown/water layer light yellow) to stand at ambient temperature overnight. Separate the layers by separatory funnel (pH of aqueous layer less than 0.8), and wash the organic layer with 200 mL deionized water. The pH of the first aqueous wash is about 2.8. Wash the organic layer a second time with 200 mL deionized water. The pH of the second aqueous wash is about 3.8. Dry the hexane layer over anhydrous magnesium sulfate and gravity filter to give an orange solution. Concentrate the solution by rotary evaporator (at 18° C. for 1.8 hours). The weight of the remaining orange-brown liquid is about 33.97 g. Vacuum distillation (most of the distillation at 8 torr) of the orange-brown organic material yielded five distillation fractions. The combined weights of the fractions and distillation pot residue is about 21.73 (64.0 percent recovery).

TABLE 1

| | | Composition of the Fractions Collected From the Distillation in Example 1a. | | | | |
|---|---|---|---|---|---|---|
| Fraction | Weight (g) | °C./torr | C$_6$H$_6$ | (3) | (4) | (5) | (6) |
| 1 | 7.10 | 32–41/80–130 | 0.024 | 0.0444 | 0.1530 | 0.1389 | 0.4383 |
| 2 | 4.90 | 82–84/8 | n.d. | n.d. | n.d. | 0.2261 | 0.5901 |
| 3 | 1.88 | 84–88/8 | n.d. | n.d. | n.d. | 0.2889 | 0.5781 |
| 4 | 2.75 | 88–98/8 | n.d. | n.d. | n.d. | 0.3483 | 0.4845 |
| 5 | 0.26 | 98–103/8 | n.d. | n.d. | n.d. | 0.3841 | 0.3391 |
| pot | 4.84 | | n.d. | n.d. | n.d. | 0.0365 | 0.0137 |

Values for compounds (3)–(6) are expressed as molar fractions and were determined under GC conditions as described below in Example 5.

(3)=trifluoroacetophenone (4)=phenyltrimethylsilane (5)=1-(4-trimethylsilylphenyl)-2,2,2-trifluoromethyl ethanone (6)=1-(3-trimethylsilylphenyl)-2,2,2-trifluoromethyl ethanone n.d.=none detected EXAMPLE 1b Larger scale preparation of
1-(3-trimethylsilylphenyl)-2,2,2-trifluoromethlly
ethanone in methylene Chloride.

Charged a 500 mL three-necked round-bottomed flask fitted with a magnetic stirring bar, thermometer (in one side arm), calcium chloride-filled drying tube (in the other side arm) and an addition funnel (in the center neck) with aluminum chloride (66.67 g, 500 mmol) and 150 mL methylene chloride. Cool the flask to −10° C. with a dry ice/ethylene glycol bath, and add trifluoroacetic anhydride (52.50 g, 250 mmol) via the addition funnel to the flask over five minutes. The reaction slurry warms to about −4° C. Rinse the dropping flask with 8 mL additional methylene chloride and add the rinse to the reaction slurry. 12 minutes after the addition is complete, the temperature of the reaction slurry increases to about +5° C. Add additional methylene chloride (35 mL) to provide better stirring. After the slurry cools to −10° C., add neat phenyltrimethylsilane (75.00 g, 500 mmol) via the addition funnel, over a 10 minute period and immediately rinse the funnel with 12 mL methylene chloride, adding this rinse to the reaction slurry. The temperature of the resulting slurry rises to about −3° C., and then falls back to −10° C. after 40–45 minutes, suggesting the presence of an exothermic reaction. Stir the reaction slurry at −10° C. for 370 minutes. At the end of the reaction, decant the brown reaction from remaining solids into a 500 mL Erlenmeyer flask. Rinse the reaction flask with 100 mL methylene chloride. Store the combined methylene chloride solutions at −18° C. overnight. Pour the organic material- (above methylene chloride solutions) into a stirred mixture of 400 g ice/water, surrounded by an ice/water bath, in such a way as to allow the temperature of the resulting mixture to reach only 13° C. Rinse the flash originally containing the organic material with 75 mL methylene chloride and add to the cold organic/aqueous slurry. Separate the organic phase (cloudy and yellow) from the aqueous phase (pH less than 0.8), and then stir the organic phase with 450 mL water for 25 minutes (at about 9° C.). Back-wash the original aqueous phase with 50 mL methylene chloride and add this to the organic/water-wash mixture. The pH of the first water wash is about 1.5. Wash the methylene chloride layer with a second portion of 450 mL fresh water and stir the resulting mixture for 25 minutes under ice/water bath cooling. The pH of the second water wash is about 2.8. Wash the methylene chloride layer with a third portion of 450 mL water and stir the resulting mixture for 25 minutes with ice/water bath cooling, The pH of the third water wash is about 3,8. Dry the resulting methylene chloride layer with anhydrous magnesium sulfate, Gravity filter the dried methylene layer and remove the solvent by rotary evaporation under vacuum (approximately 20 torr at 13° C.) to provide a dark orange/brown oil (59.30 g). Vacuum distillation (approximately 8 torr) of the orange/brown organic material after rotary evaporation provides 9 fractions, The combined weights of the fractions and distillation pot residue are about 57.53 (97.0 percent recovery),

TABLE 2

Composition of the Fractions Collected from the Distillation in Example 1b.

| Fraction | Weight (g) | °C./torr | (3) | (5) | (6) |
|---|---|---|---|---|---|
| 1 | 4.61 | 22–47/8 | 0.9790 | 0.0050 | 0.0154 |
| 2 | 6.10 | 43–74/8 | 0.9111 | 0.0218 | 0.0655 |
| 3 | 7.12 | 74–85/8 | 0.0859 | 0.2172 | 0.6809 |
| 4 | 6.04 | 85–85/8 | 0.0063 | 0.2520 | 0.7222 |
| 5 | 8.67 | 85–87/8 | 0.0040 | 0.2831 | 0.6874 |
| 6 | 6.46 | 87/8 | 0.0008 | 0.3296 | 0.6358 |
| 7 | 6.86 | 87–89/8 | n.d. | 0.3976 | 0.5384 |
| 8 | 3.71 | 89–104/8 | n.d. | 0.4882 | 0.3097 |
| 9 | 0.89 | 104–117/8 | n.d. | 0.3261 | 0.0707 |
| pot | 7.07 | | n.d. | 0.0025 | n.d. |

Values for compounds (3)–(6) are expressed as molar fractions and were determined under GC conditions as described below in Example 5.

(3)=trifluoroacetophenone (5)=1-(4-trimethylsilylphenyl)-2,2,2-trifluoromethyl ethanone (6)=1-(3-trimethylsilylphenyl)-2,2,2-trifluoromethyl ethanone

EXAMPLE 2

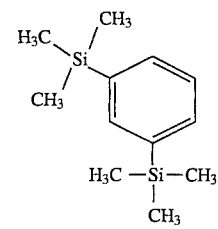

Preparation of 1,3-bis(Trimethylsilyl)benzene.

Charge a 100 mL three-neck round-bottom flask (which contains a magnetic stir bar and which was fitted with calcium chloride drying tube in one side neck, a thermometer in the other side neck and a white rubber septum in the middle neck—with a :syringe needle, attached to a nitrogen line, through the septum) with 1,3-dibromobenzene (2.36 g, 10 mmol, 3.7 g.c. area percent 1,4-isomer/96.3 area % 1,3-isomer), tetrahydrofuran (THF-15 mL), triethylamine (about 0.1 g) anti chlorotrimethylsilane (2.80 mL, 22 mmol). Add the chlorotzrimethylsilane by syringe. Rinse the syringe with another 15 mL THF and add the rinse to the reaction solution). Stir the resulting solution was stirred by magnetic bar. Place a dry ice/acetone bath under the reaction flask and apply a gentle stream of nitrogen through the flask, cooling the contents of the flask to −70° C. Add over a period of 18 minutes an n-butyllithium/hexane solution (13.75 mL, 22 mmol) by syringe through the rubber septum, maintaining the temperature of the reaction mixture below −60° C. during the entire addition. After the addition is complete, stir the reaction mixture (liquid, with small amount of white solids) at −60° to −70° C. for an additional 30 minutes. Remove the cold bath and allow the contents of the reaction flask to warm to 19° C. over a period of 25 minutes (with stirring and nitrogen atmosphere). During the warming more white precipitate falls out of the reaction solution. After a total of 30 minutes of warming (reaction mixture at 20.5° C.) add 20 mL methylene chloride to the reaction mixture.

Gravity filter the resulting slurry through fluted filter paper, to obtain a clear, water-white filtrate. Rinse the residue in the reaction flask with another 15 mL of methylene chloride and filter the rinse. Concentrate the combined filtrates by rotary evaporator (approximately 21 mm Hg at 44° C.). The residue is a mixture of clear oil and white solids. Extract the residue into 20 mL methylene chloride. Gravity filter the resulting slurry through fluted filter paper, to obtain a clear, water-white filtrate. The white solids are soluble in water. Concentrate the filtrate by rotary evaporator (approximately 22 mm Hg at 37° C.) to provide a slurry of clear oil and white solids (weight 2.00 g). Extract this residue into 25 mL hexanes. Gravity filter the resulting slurry through fluted filter paper, to obtain a clear, water-white filtrate. The remaining solids are again soluble in water. Concentrate the filtrate by rotary evaporator (approximately 22 mm Hg at 38° C.) to leave 1.58 g of clear, water-white oil, with no solids. Gas chromatography analysis (area percents): 1,3-bis(trimethylsilyl)benzene 94.3%, $R_t$=7.04 minutes, 67.1 percent yield from 1,3-dibromobenzene), 1,4-bis(trimethylsilyl)benzene (4.8%, $R_t$=8.05 minutes) and phenyltrimethylsilane (0.9%); bp of title compound=112° C. at 22 mm Hg; estimated bp=110° C. at 20 torr and 220° C. at 760 torr.

EXAMPLE 3

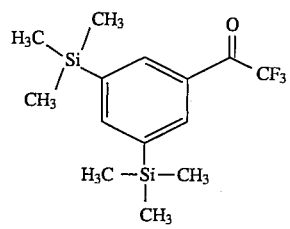

Preparation of
3,5-bis(Trimethylsilyl)trifluoroacetophenone.

Charge a 100 mL three-necked round-bottomed flask containing a magnetic stir bar with aluminum chloride (2.00 g, 15 mmol) and 30 mL methylene chloride. Cool the flask with a dry ice/ethylene glycol bath to below −10° C. Add a solution of trifluoroacetic anhydride (1.10 g, 5.5 mmol) in 10 mL methylene chloride to the reaction flask, and re-cool the resulting slurry to −10° C. Add a solution of 1,3-bis(trimethylsilyl)benzene (1.16 g,, 4.8 mmol, unpurified, prepared in example 4) in 10 mL methylene chloride over one minute to the stirred and chilled reaction slurry. Stir the reaction at −12° C. for 500 minutes. [This procedure also provides 1-(3-trimethylsilylphenyl)-2,2,2-trifluoromethyl ethanone.] GC analysis of of the reaction provides the following composition of the reaction:

TABLE 3

Composition of End Reaction of Example 3.

| Compound | Molar Fraction |
| --- | --- |
| Benzene | 0.1986 |
| Trifluoroacetophenone | 0.0940 |
| Phenyltrimethylsilane | 0.0824 |
| 1-(3-trimethylsilylphenyl)-2,2,2-trifluoromethyl ethanone (title compound of example 1, 1a and 1b) | 0.2111 |
| 1-(4-trimethylsilylphenyl)-2,2,2-trifluoromethyl ethanone | 0.0518 |

TABLE 3-continued

Composition of End Reaction of Example 3.

| Compound | Molar Fraction |
| --- | --- |
| 1,3-bis(Trimethylsilyl)benzene | 0.0081 |
| 1,4-bis(Trimethylsilyl)benzene | 0.0043 |
| 3,5-bis(Trimethylsilyl)trifluoroacetophenone (title compound of example 3) | 0.3497 |

Molar fraction values determined by GC under conditions described below in Example 5.

EXAMPLE 4

Separation of
1-(3-Trimethylsilylphenyl)-2,2,2-Trifluoromethyl
Ethaneone from Related Products by Distillation The relative votatilities of 1-(3 -trimethylsilylphenyl)-2,2,2-trifluoromethyl ethanone compared to the two related products of this invention are as follows (expressed as the ratio of volatilities of the more volatile component to the less volatile component):

Relative Volatility of trifluoroacetophenone over 1-(3 -trimethylsilylphenyl)-2,2,2-trifluoromethyl ethanone=11.1

Relative Volatilty of 1-(3-trimethylsilylphenyl)- 2,2,2-trifluoromethyl ethanone over 1-(4-trimethylsilylphenyl)-2, 2,2-trifluoromethyl ethanone=1.60

1-(3-Trimethylsilylphenyl)-2,2,2-trifluoromethyl ethanone can be separated from the two related products by distillation, for example employing the following procedure. A 31/32 inch jacketed and silvered column is packed with 69 inches of 1 inch diameter, 316 stainless steel High Goodloe 773 structured packing. The column is fitted with an adiabatic jacket, composed of an inner layer of 1 inch fiber glass wrapped with heat tape in an upper and lower zone and is finally covered with 2 inch fiber glass insulation. The magnetic reflux splitting head is controlled by a reflux timer and is fitted with a standard thermometer for monitoring overheads temperature. Vacuum is supplied by a system composed of a Hyvax™ 7 pump, protected by a dry ice trap, and fitted with a McLeod gage for monitoring the overheads pressure. The 2 L distillation pot is heated with an electric mantle, agitated magnetically, and fitted with a mercury manometer for monitoring bottoms pressure and with a thermocouple for monitoring bottoms temperature. This column is rated at 7.3 theoretical stages, or 11.6 transfer units.

The still pot is charged with a solution of the composition: 219.5 g of trifluoroacetophenone, 522.5 g of 1-(3-trimethylsilylphenyl)-2,2,2-trifluoromethyl ethanone and 258.5 g of 1-(4-trimethylsilylphenyl)-2,2,2-trifluoromethyl ethanone. The solution is heated to total reflux at 20 mm Hg pressure until the column is equilibrated. The reflux ratio is established at 0.4. A total of 211.8 g of distillate is removed, to a final overheads temperature of 60.2° C., with a composition of 211.6 g trifluoroacetophenone and 0.2 g of the two higher boiling components. The bottoms composition is 7.9 g of trifluoroacetophenone and 780.8 g of the two higher boiling components. The reflux ratio is changed to 8.0, and 7.5 g of distillate is removed, to a final overheads temperature of 63.3° C., with a composition of 7.1 g trifluoroacetophenone and 0.4 g of the two higher boiling components. The bottoms concentration after the second part of the distillation is 780.4 g of the two higher boiling components and 0.8 g of trifluoroacetophenone.

The bottoms solution is distilled through a column similar to that described above, except that it is packed with 144 inches of 1 inch diameter, 316 stainless steel High Goodloe 773 structured packing. This column is rated at 36.0 theoretical stages, or 57.2 transfer units. The solution is heated to total reflux at 20 mm Hg pressure until the column is equilibrated. The reflux ratio is established at 8.0. The distillation is run until the temperature of the overheads reach 128° C. A total of 522.0 g of distillate is removed, with a composition of 521.5 g of 1-(3-trimethylsilylphenyl)-2,2,2-trifluoromethyl ethanone and 0.5 g of 1-(4-trimethylsilylphenyl)-2,2,2-trifluoromethyl ethanone. The bottoms composition is 0.5 g of 1-(3-trimethylsilylphenyl)-2,2,2-trifluoromethyl ethanone and 257.4 g of 1-(4-trimethylsilylphenyl)-2,2,2-trifluoromethyl ethanone.

EXAMPLE 5

The compounds of this invention can be separated and isolated from the quenched reaction mixture or further separated from the fractions collected during distillation by gas chromatography. Table 5 sets forth the retention times of the compounds under Method A or Method B. A Chrompak #7452 column is used (CP-Sil 8 CB; 95% dimethyl, 5% phenyl; 25 m×0.32 mm I.D.; 0.25 μm film thickness).

TABLE 5

Gas Chromatography (GC) Retention Times For Compounds Described in Examples 1–4.

| Compound | Method A $R_t$ (min) | Response Factor (Method A) | Method B $R_t$ (min) | Response Factor (Method B) |
|---|---|---|---|---|
| 7 | 1.02 | | 0.70 | |
| 8 | | | 0.90 | |
| 9 | | | 1.31 | 1.660 |
| 10 | | | 1.91 | |
| 3 | 1.60 | 1.638 | 4.24 | 1.625 |
| 4 | 2.46 | 1.101 | 6.25 | 1.094 |
| 11 | 2.66 | 1.57[a] | 6.55 | 1.45[a] |
| 6 | 4.94 | (1.000) | 9.23 | (1.000) |
| 5 | 5.46 | (1.000)[b] | 9.65 | (1.000)[b] |
| 12 | 6.84 | 0.816 | 10.66 | 0.832 |
| 13 | 7.86 | 0.806 | 11.33 | 0.800 |
| 14 | 9.63 | 0.70[a] | 12.38 | 0.70[a] |

Method A
Starting temperature = 80° C.
Hold time = 0 min
Ramp = 50° C./min
Final temperature = 250° C.

Method B
Starting temperature = 40° C.
Hold time = 2 min
Ramp = 10° C./min
Final temperature = 250° C.

a) Estimated response factor.

b) Assumed the same as for 1-(3-trimethylsilylphenyl)-2,2,2-trifluoromethyl ethanone.
(3)=trifluoroacetophenone
(4)=phenyltrimethylsilane
(5)=1-(4-trimethylsilylphenyl)-2,2,2-trifluoromethyl ethanone
(6)=1-(3-trimethylsilylphenyl)-2,2,2-trifluoromethyl thanone
(7)=trifluoroacetic anhydride
(8)=methylene chloride
(9)=benzene
(10)=trifluoroacetic acid
(11)=1,3-bis(trifluoroacetyl)benzene
(12)=1,3-bis(trimethylsilyl)benzene
(13)=1,4-bis(trimethylsilyl)benzene
(14)=3,5-bis(trimethylsilyl)-trifluoroacetophenone

What is claimed is:

1. A process for preparing a compound of the formula:

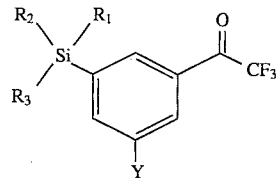

wherein
$R_1$, $R_2$ and $R_3$ are each independently $C_1$–$C_4$ alkyl; and
Y is hydrogen or —$SiR_1R_2R_3$, comprising reacting a compound of the formula:

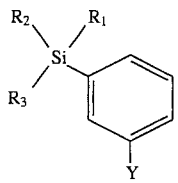

wherein $R_1$, $R_2$, $R_3$ and Y are defined as above, with a trifluoroacylating agent in the presence of a Friedel-Crafts acylating catalyst.

2. A process according to claim 1 wherein the trifluoroacylating agent is trifluoroacetic anhydride.

3. A process according to claim 2 wherein the Friedel-Crafts acylating catalyst is aluminum chloride.

4. A process according to claim 3 wherein $R_1$, $R_2$ and $R_3$ are methyl and Y is hydrogen.

5. A process according to claim 1 wherein the trifluoroacylating agent is trifluoroacetyl chloride.

* * * * *